United States Patent [19]

Martinez

[11] 4,246,902
[45] Jan. 27, 1981

[54] SURGICAL CUTTING INSTRUMENT

[76] Inventor: Miguel Martinez, 6006 Hunt Ridge Rd., Baltimore, Md. 21210

[21] Appl. No.: 885,523

[22] Filed: Mar. 10, 1978

[51] Int. Cl.³ .................................. A61B 17/32
[52] U.S. Cl. .................... 128/305; 128/276
[58] Field of Search ............ 128/305, 276, 2 B, 274, 128/751, 752, 755; 251/343, 344, 342; 30/208, 209, 210, 241

[56] References Cited

U.S. PATENT DOCUMENTS

| | | | |
|---|---|---|---|
| 3,561,429 | 2/1971 | Jewett | 128/2 B |
| 3,815,604 | 6/1974 | O'Malley et al. | 128/305 |
| 3,882,872 | 5/1975 | Douvas et al. | 128/305 |
| 3,977,409 | 8/1976 | Brendling | 251/342 X |
| 4,108,182 | 8/1978 | Hartman et al. | 128/305 |
| 4,167,943 | 9/1979 | Banko | 128/752 |

*Primary Examiner*—Robert W. Michell
*Assistant Examiner*—Michael H. Thaler
*Attorney, Agent, or Firm*—Robert H. Epstein

[57] ABSTRACT

A surgical cutting instrument, particularly useful for ophthalmic surgery, includes an elongate probe formed of an outer tubular member having an aperture in the distal end thereof and an inner cutting member having a peripheral cutting edge at the distal end thereof and an elongate body with an opening running therealong and carrying a piston disposed in a chamber of a hub through which the inner cutting member extends and which communicates with a source of suction, a drive unit for reciprocating the inner cutting member relative to the outer member, the opening along the inner cutting member forming an increased cross sectional flow area for cut substances being withdrawn by suction and the relative reciprocation of the inner and outer members coupled with increasing and decreasing pressure from the piston agitating the cut substances to prevent clogging of the probe. A finger-operated valve is formed of an elastic tubing stretched over the closed end of a rigid tube communicating with the chamber of the hub, the rigid tube having an opening in a side wall adjacent the closed end, which opening is normally sealed by the elastic tubing and can be opened by applying a force to the tubing at a position opposite the opening.

12 Claims, 10 Drawing Figures

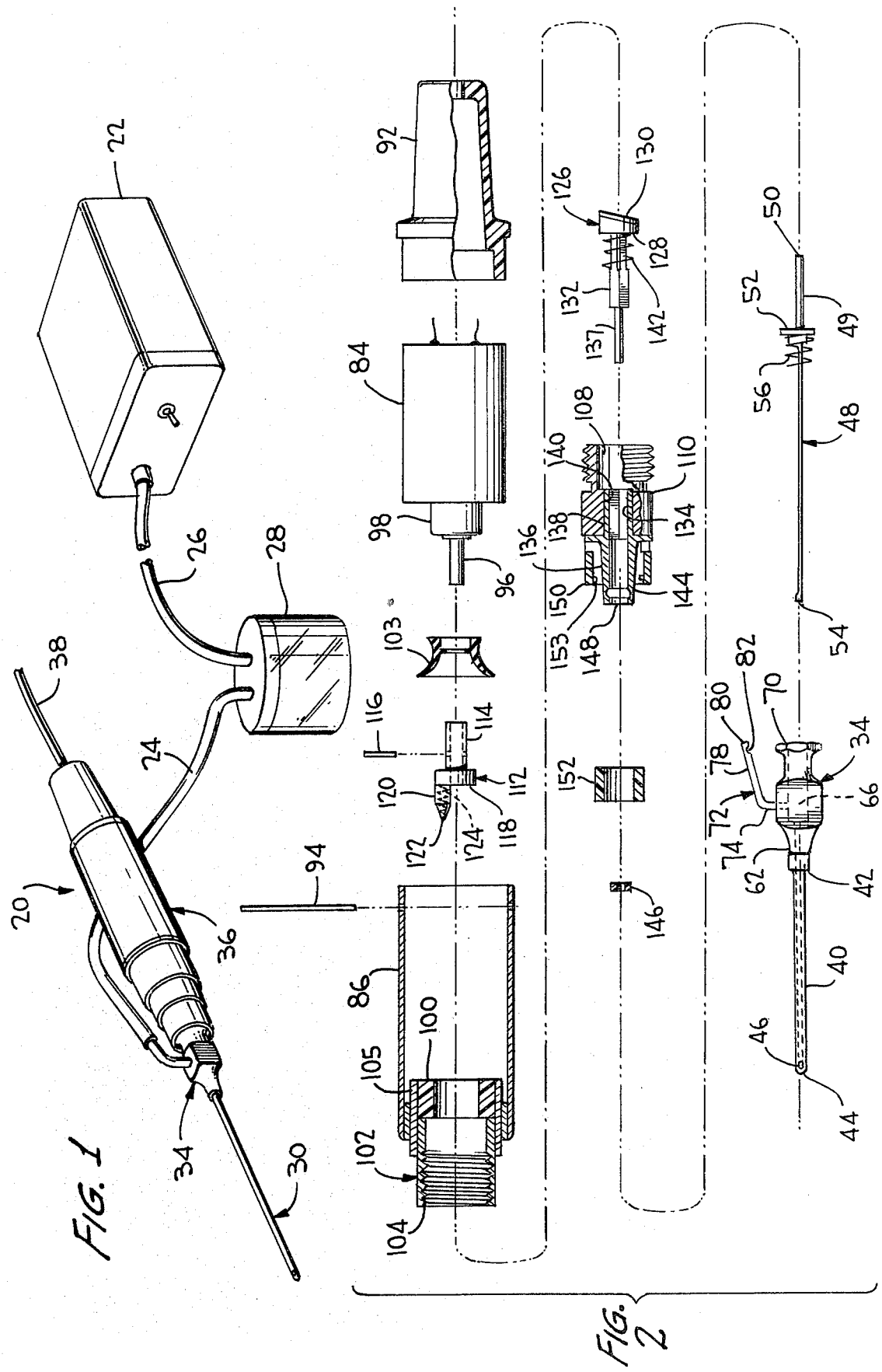

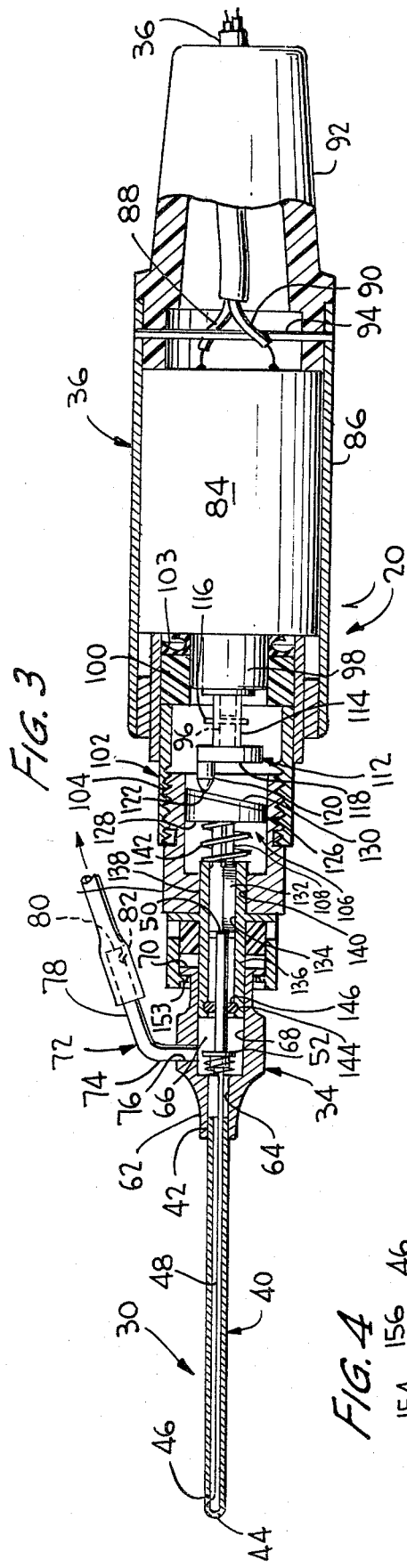
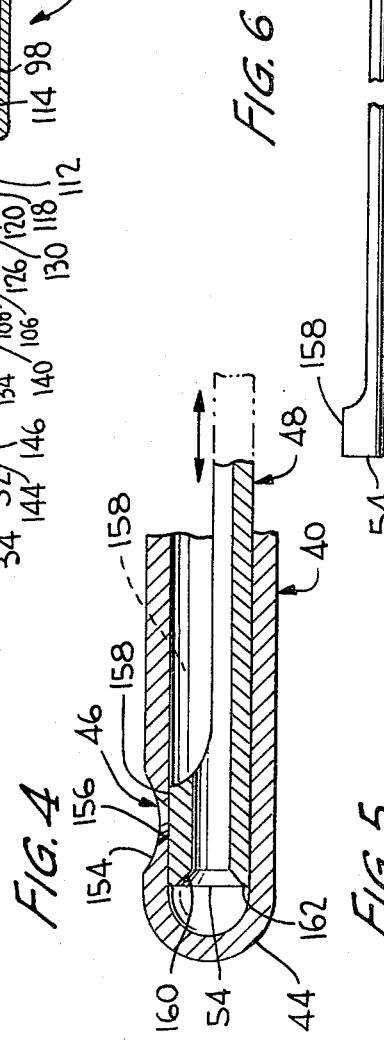
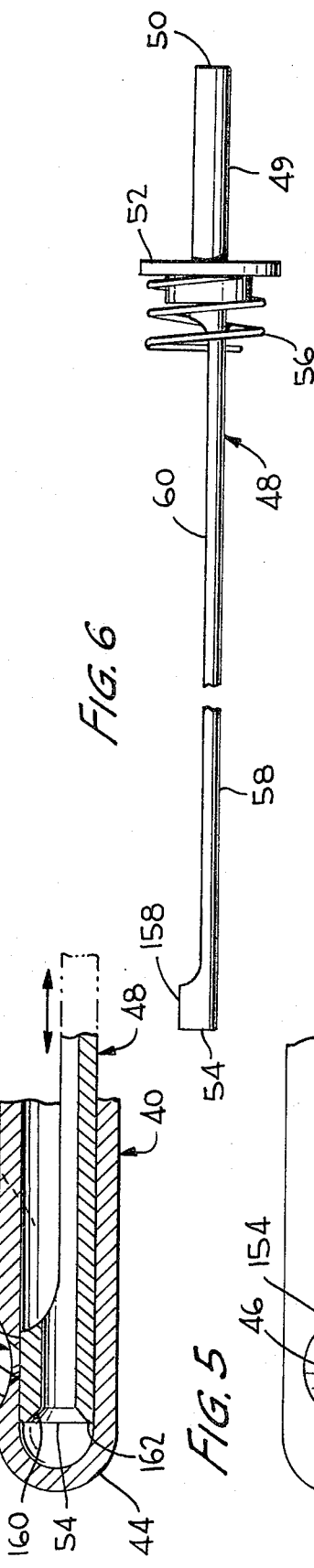
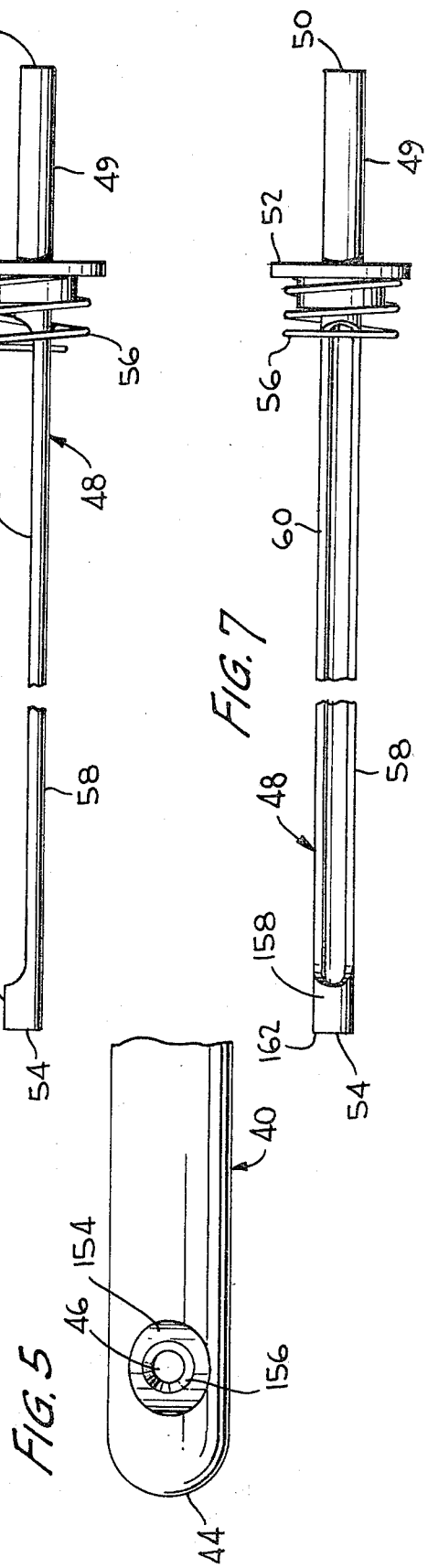
FIG. 3  FIG. 4  FIG. 5  FIG. 6  FIG. 7

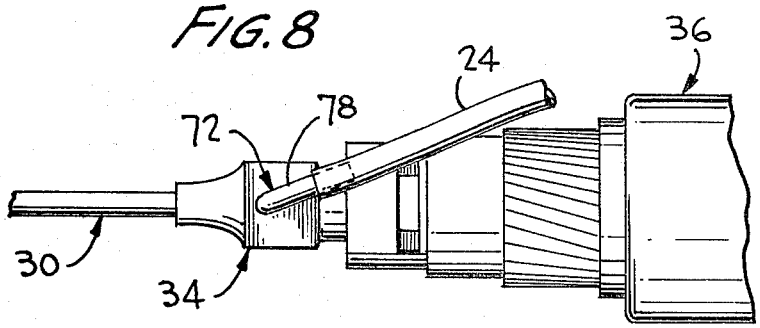
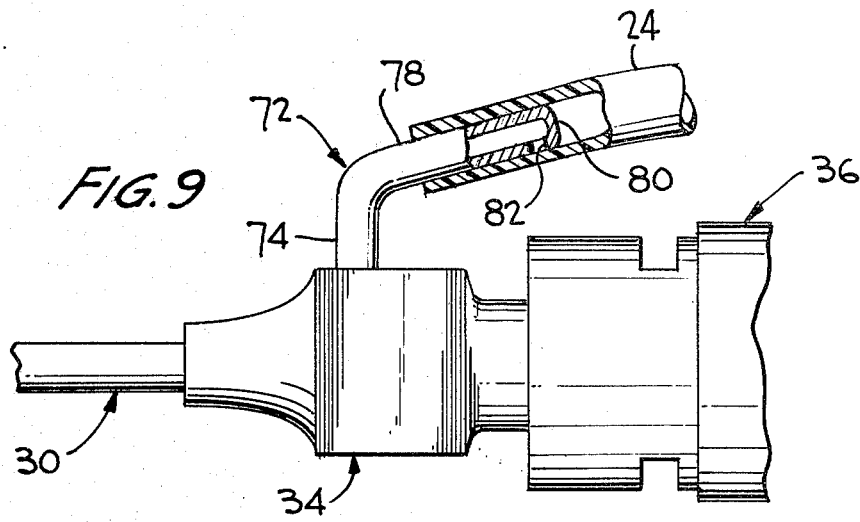
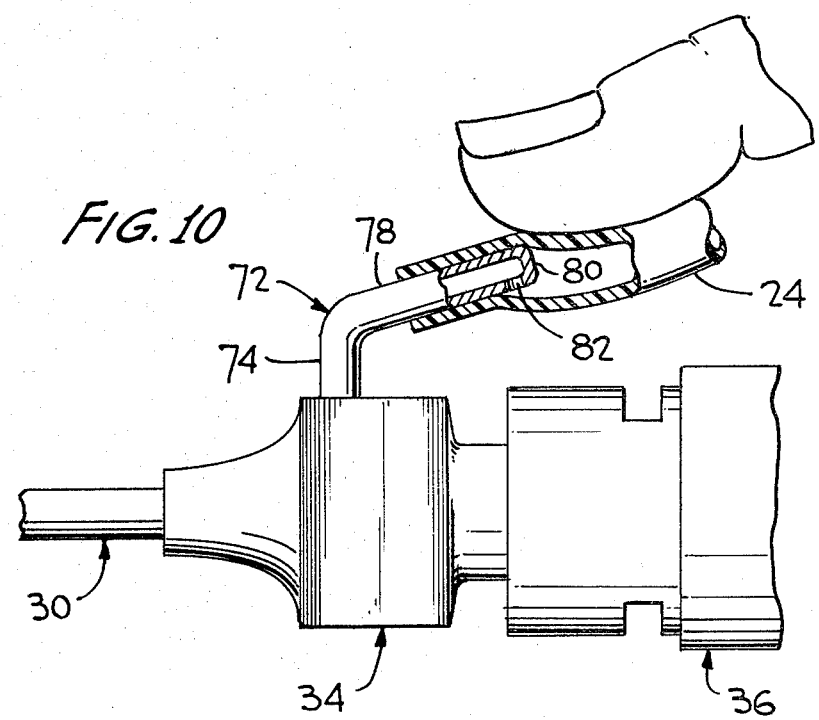

SURGICAL CUTTING INSTRUMENT

BACKGROUND OF THE INVENTION

1. Field of the Invention

The present invention pertains to surgical instruments and, more particularly, to a surgical cutting instrument for use in cutting and evacuating material from parts and organs of animal and human bodies.

2. Discussion of the Prior Art

Recently, surgical instruments have been designed to aid ophthalmic surgeons in removing vitreous, blood clots cataracts, lenses and other matter from the eye. Such instruments have utilized pulsating fluid jets, as exemplified by U.S. Pat. Nos. 3,732,858 and 3,996,935 to Banko and Nos. 3,930,505 and 4,024,866 to Wallach, or mechanical cutting or shearing mechanisms, such as reciprocating members, as exemplified by U.S. Pat. No. 3,776,238 to Peyman et al, No. 3,884,238 to O'Malley et al, No. 3,994,297 to Kopf and No. 4,011,869 to Seiler, Jr., or rotating members, as exemplified by U.S. Pat. No. 3,732,858 to Banko, No. 3,734,099 to Bender et al, No. 3,882,872 to Douvas et al, No. 3,844,272 to Banko, No. 3,906,954 to Baehr et al, No. 3,945,375 to Banko, No. 3,976,077 to Kerfoot, Jr., No. 3,990,453 to Douvas et al, and No. 4,002,169 to Cupler II. The prior art surgical instruments, as exemplified by the above noted patents, have been well received in general; however, the prior art surgical instruments have the disadvantages of being quite expensive since they have been invariably constructed of specially designed cutting members requiring detailed machining and specially designed coupling assemblies, of providing inadequate suction due to suction line losses and the restricted cross sectional flow area of the probe of the instrument which desirably has a very small diameter, on the order of 0.005 inch, and of being awkward to handle due to their size and the precise suction control required. In other words, while prior art surgical cutting instruments have the potential for facilitating various surgical operations on the eye and other portions of the body, that potential has, as yet, not been fulfilled since, optimally, such instruments should be easy to handle and operate while permitting precision cutting and suction control and being relatively trouble free, and the prior art surgical cutting instruments have not had these attributes. A particular trouble spot in prior art surgical cutting instruments is that they frequently become clogged with cut tissue during surgical procedures therefore requiring the probe to be removed from the incision to permit cleaning thereof or insertion of a new probe.

SUMMARY OF THE INVENTION

Accordingly, it is a primary object of the present invention to overcome the above mentioned disadvantages of the prior art by constructing a surgical cutting instrument in a simple, inexpensive manner while providing precision cutting and suction control characteristics.

More particularly, it is a primary object of the present invention to provide an opening along an inner cutting member of an elongate probe such that the cross sectional flow area of the probe is increased and reciprocation of the inner cutting member agitates cut substances to facilitate evacuation of the cut substances without clogging of the probe.

Another object of the present invention is to reciprocate a piston in a chamber of a hub mounting an elongate probe of a surgical cutting instrument to increase and decrease pressure in the probe to prevent clogging by cut substances.

A further object of the present invention is to form a rotary-to-reciprocating motion translating mechanism for a surgical cutting instrument of a cam having a nib projecting therefrom at a position offset from its axis of rotation, a ball bearing carried by the nib and a cam follower having a planar surface contacting the ball bearing and arranged at an angle other than 90° to the axis of rotation of the cam.

The present invention has another object in the use of a finger-operated valve to control suction applied to a surgical cutting instrument, the valve including a rigid tube having a closed end with an opening in a side wall adjacent the closed end and an elastic tubing, preferably made of silicone rubber, stretched over the closed end of the rigid tube to normally seal the opening and being flexed by application of force thereto at a position opposite the opening to permit flow through the opening.

An additional object of the present invention is to extend an inner cutting member of an elongate probe of a surgical cutting instrument beyond a hub mounting the probe to be received in a hollow end of a reciprocating driving member to maintain the inner cutting member in axial alignment and to adjust and support the inner cutting member in the probe with structural continuity.

Yet a further object of the present invention is to configure an aperture in the tip of an outer tubular member of a probe of a surgical cutting instrument to have a cylindrical surface formed by cross grinding to reduce the thickness of the outer member at the aperture to allow a cutting edge within the outer member to be positioned closer to tissue to be cut, to direct tissue to be cut inwardly and to define a cutting area along the distal edge of the surface, the aperture having a conical bore centered in the cylindrical surface to provide a round port for equalizing suction force on tissue with the taper providing an ideal cutting angle for shearing tissue.

Some of the advantages of the present invention over the prior art are that the surgical cutting instrument of the present invention minimizes clogging and jamming of the probe, is easy to manipulate both for cutting and suction control, is simple in construction and, correspondingly, relatively inexpensive to manufacture and combines precision cutting with structural stability.

The present invention is generally characterized in a surgical cutting instrument including an elongate probe including a tubular outer member having a distal end with an aperture in a side wall thereof, and an inner cutting member slidably disposed in the outer member having a distal end defining a cutting edge positioned at the distal end of the outer member and an elongate body extending from the distal end of the inner cutting member and having an opening running therealong, a drive unit for reciprocating the inner cutting member and the outer member relative to each other to move the cutting edge of the inner cutting member back and forth past the aperture in the outer member, and suction means communicating with the probe to remove substance cut by relative reciprocating of the inner cutting member and the outer member whereby the opening along the elongate body of the inner cutting member provides increased cross sectional flow are a along the probe and causes relative reciprocation of the inner cutting member and the outer member to agitate the cut substance to prevent clogging of the probe.

Other objects and advantages of the present invention will become apparent from the following discussion of the preferred embodiment taken in conjunction with the accompanying drawings.

BRIEF DESCRIPTION OF THE DRAWINGS

FIG. 1 is a perspective view of a surgical cutting instrument and a suction system according to the present invention.

FIG. 2 is an exploded view of the surgical cutting instrument of FIG. 1.

FIG. 3 is a longitudinal cross section of the surgical cutting instrument of FIG. 1.

FIG. 4 is a broken section of the cutting tip of the surgical cutting instrument of FIG. 1.

FIG. 5 is a broken plan view of the cutting tip of the surgical cutting instrument of FIG. 1.

FIGS. 6 and 7 are side and plan views, respectively, of the inner cutting member of the surgical cutting instrument of FIG. 1.

FIG. 8 is a top plan view of a finger-operated suction control valve for the surgical cutting instrument of FIG. 1.

FIGS. 9 and 10 are side views, partly in section, of the suction control valve of FIG. 8 in closed and open positions, respectively.

DESCRIPTION OF THE PREFERRED EMBODIMENT

A surgical cutting instrument 20 according to the present invention is shown in FIG. 1 connected with a suction pump 22 of any suitable structure via flexible tubings 24 and 26 communicating with a collection receptacle 28. The surgical cutting instrument 20 has, as basic components, an elongate probe 30 extending from a hub 34 which is detachably mounted on a drive unit 36 supplied with electricity via a wire 38 adapted to be connected with any suitable source of electricity.

As best shown in FIGS. 2 and 3, the probe 30 includes an outer, elongate, and tubular member 40 having a proximal end 42 secured to hub 34, a distal end 44 disposed at the cutting tip of the probe and an aperture 46 in the side wall of the outer member 40 adjacent the distal end 44. An inner, elongate cutting member 48 is slidably disposed within outer member 40 and has a stem 49 extending through the hub 34 and terminating at a proximal end 50, a piston 52 attached to the stem at a position spaced from the proximal end, a distal end 54 arranged at the tip of the probe 30 and a coiled spring 56 mounted on the piston 52. As best shown in FIGS. 6 and 7, the inner member 48 has an elongate body 58 extending between piston 52 and distal end 54 with a majority of the length of the body 58 cut away to form an elongate opening 60 running therealong. The stem 49 and body 58 can be made of one piece of tubular material; however, the stem 49 need not be hollow thereby permitting the stem to be formed of a solid rod secured to piston 52.

The hub 34 has a neck 62 defining a passage 64 in which the proximal end 42 of outer member 40 is secured, and the passage 64 communicates with a chamber 66 having a truncated, slightly conical configuration defined by a wall 68 of the hub, the external configuration of the hub being substantially the same as that of conventional hypodermic needles to provide a Luer-Loc type connection permitting components to be attached to a flange at an open rear end 70 thereof. The diameter of chamber 66 is only slightly larger than the diameter of piston 52 such that the piston 52 functions to alternately increase and decrease pressure in the probe during operation of the surgical cutting instrument 20, as will be described in more detail hereinafter.

An L-shaped, rigid, suction tube 72 has a lower leg 74 extending through a bore 76 in hub 34 to communicate via an open end thereof with chamber 66 and an upper leg 78 extending at an angle slightly greater than 90° from the lower leg and terminating at a closed end 80. An opening 82 is formed in a side wall of upper leg 78 adjacent closed end 80 to permit communication with tubing 24, which is preferably made of an elastic, resilient material such as silicone rubber of a diameter slightly less than the outside diameter of the closed end of the suction tube 72 to permit the tubing 24 to be stretched over the closed end 80 to cover and seal the opening 82 and form a finger-operated, suction control valve.

The drive unit 36 includes an electric motor 84 disposed in a cylindrical casing 86 receiving electricity via leads 88 and 90 of wire 38 which pass through an end cap 92 held in the housing 86 by a pin 94. The motor 84 has a rotatably driven shaft 96 extending from a bearing housing 98 which is snuggly received in an annular mount 100 of resilient material disposed in a sleeve 102 secured to the front of the casing 86, a flexible seal 103 of resilient material being arranged around bearing housing 98 between the mount 100 and the motor. The sleeve 102 has a cylindrical, internally threaded end 104 which is secured to a cylinder 105 mounted in the casing 86 and housing the mount 100 and the seal 103.

A rotating-to-reciprocating motion translating mechanism 106 is mounted in a chamber 108 in a coupling member 110 which is externally threaded to engage the internal threads in the end 104 of sleeve 102. The motion translating mechanism 106 includes an eccentric cam 112 having a hollow shaft 114 telescoping over the shaft 96 of the motor and coupled therewith by a pin 116 such that the cam 112 rotates with the shaft 96. The cam 112 has a plate 118 axially secured to hollow shaft 114, and a nib 120 projects from plate 116 at a position displsed from the center of the plate, the nib being filled with oil and carrying a ball 122 rotatably mounted at the end thereof and biased toward the end by a coiled spring 124 seated in the nib. A cam follower 126 includes a plate 128 having a planar surface 130 arranged at an angle other than 90° to the longitudinal axis of the hollow shaft 114 of cam 112, a shaft 132 extending from plate 128 and having a square configuration in cross section to be received in a passage 134 of mating configuration in a coupling 136 such that the cam follower is prevented from rotating, and a hollow end 137 axially extending from shaft 132 to receive the stem 49 of inner cutting member 48. Of course, any suitable flat sided configuration can be used for shaft 132 and passage 134 so long as rotation is prevented and axial, reciprocating, sliding movement is permitted. The coupling 136 has a stub 138 defining passage 134 press fit in an axial bore 140 in coupling member 110, and a coiled spring 142 is mounted in compression between the end of stub 138 and plate 128 to force the cam follower 126 toward the cam 112 and assure that the angled surface 130 bears against the ball 122. The coupling 136 has a nose 144 with an external conical configuration to be press fit in the rear end 70 of hub 34, and an annular bushing 146 is seated in an annular recess 148 in the end of nose 144 to provide sealing contact with the hollow end 137 of shaft 132. The coupling 136 has an outer wall 150 spaced from nose 144, and an annular seal 152 is disposed in the annular space between nose 144 and wall 150 such that seal 152 along with bushing 146, which are both made of a soft resilient material, such as silicone rubber, effectively seal the drive unit 36 from the probe 30 to protect the drive unit from fluids encountered or used during surgical operations. The outer wall 150 engages the flange at the end 70 of hub 34 in Luer-Loc fashion and carries interrupted threads 153 to clamp the drive unit to the hub while permitting the hub to be rotated relative to the drive unit.

The structure of the tip of probe 30 is shown in greater detail in FIGS. 4 and 5 wherein it can be seen that the aperture 46 in the distal end of outer member 40 has a curved surface 154 formed as a portion of a cylinder having an axis extending transverse to but spaced from the longitudinal axis of outer member 40 and a conical bore 156 tapering internally of the outer member from surface 154. The cut-away portion 60 of inner member 48 terminates at a position spaced from the distal end 54 to define a cylindrical cutting head 158, and the open distal end 54 is conically bored to define an inwardly tapered surface 160 adjacent a peripheral cutting edge 162.

In operation, the surgical cutting instrument 20 is connected with suction pump 22 via tubing 24, collection receptacle 28 and tubing 26 such that vacuum can be created in the probe 30 via suction tube 72 and chamber 68, and electricity is supplied to motor 84 under the control of a switch (not shown) to rotate driven shaft 96. The rotation of shaft 96 rotates cam 112 thereby causing cam follower 126 to reciprocate due to the action of spring 142 forcing surface 130 against ball 122 in eccentrically mounted nib 120 while the cam follower is prevented from rotating due to the square shaft 132 received in the square passage 134. The reciprocation of cam follower 126 is imparted to inner member 48 by the hollow end 137 of the cam follower engaging piston 52, the inner member 48 following the reciprocation of the cam follower by means of the spring 56 forcing the piston 52 into engagement with the hollow end 137 of the cam follower.

The probe 30 is inserted in an incision in the eye or other area of the body while no suction is supplied to the probe due to the tubing 24 sealing opening 82, as shown in FIG. 9. The rotating Luer-Loc engagement of the end flange 70 of the hub 34 with the threads 153 on wall 150 of coupling 136 permits the positioning of aperture 46 in the distal end of the probe at the proper visual angle for the surgeon and also permits proper positioning of the finger-operated valve. The suction tube 72 can be rotated slightly such that arm 78 is disposed at a slight angle to the longitudinal axis of the surgical cutting instrument, as shown in FIG. 8, to be more easily manipulated with a finger of either the right hand or the left hand, in the latter case the suction tube being turned slightly clockwise looking at FIG. 8.

Once the probe 30 is inserted in the body, electricity supplied to motor 84 causes inner member 48 to reciprocate, as described above, thereby causing cutting head 158 to move back and forth across aperture 46 between the positions shown in solid and dashed lines in FIG. 4. When the cutting head is in the dashed line position, suction causes the substance or tissue to be cut to be drawn into aperture 46; and, when the cutting head is moved to the solid line position, the peripheral cutting edge 162 will sever the substance with a shearing action. The cut substance is withdrawn from the probe by suction applied via tube 72, the cut substance passing through the cylindrical head 158 and along body 58 to chamber 68 in the hub. The opening 60 in the body of inner member 48 increases the cross sectional flow area to facilitate the removal of the cut substance from the probe 30 without correspondingly increasing the outer diameter of the probe and, additionally, causes agitation of the cut substance due to the relative reciprocation of the inner and outer members producing shear stresses on the fluid column of cut substance. Flow of the cut substance through the probe is also enhanced by the movement of piston 52 in chamber 68 which produces a forward and backward motion to the fluid column of cut substance due to alternating increasing and decreasing pressure to thereby continuously maintain movement of the cut substance.

The increased cross sectional flow are a and the agitation produced by the opening 60 in the inner member coupled with the pressure from piston 52 minimize clogging of the probe by the cut substance; however, should the inner member become jammed by clogging or tissue entrapment or should the probe require cleaning or sharpening, the probe can be easily disassembled by merely releasing the engagement of end flange 70 with coupling 136 and pulling the inner member out of the outer member by grasping stem 49 which protrudes from the hub 34.

Suction supplied to the probe 30 can be easily controlled by the surgeon via the finger-operated valve in that the tubing 24 will normally seal the opening 82 to close the valve, as shown in FIG. 9, due to the elasticity of the silicone rubber. When it is desired to apply suction to the probe, the surgeon applies a fingertip force to the tubing opposite the opening 82 at the closed end 80 of the suction tube and such force causes the tubing 24 to flex, as shown in FIG. 10, to open the port 82 and establish communication between the suction pump and the probe. By introducing the vacuum at the chamber 68 in the hub, residual vacuum which could cause tissue to adhere to the aperture 46 in the distal end of outer member 40 is reduced due to the proximity of the finger-operated valve to the tip of the probe.

The probe 30 is extremely small in diameter with the outer diameter of the outer member 40 being normally about 0.005 inch and the outer diameter of the inner member 48 being substantially equal to the inner diameter of the outer member, normally about 0.004 inch. Preferably, the outer and inner members are made of stainless steel and, for example, can be formed of 19 gauge and 21 gauge tubes, respectively. Further, for example, the length from the distal end of the outer member to the hub 34 may be 30 mm while the length of the inner member may be 40 mm to cause the stem 49 to protrude from the hub, the cutting head 158 being 1 mm in length and the opening 60 being 36 mm in length. The presence of opening 60 coupled with normal production variations of 0.005 inch permits the inner diameter of the outer member to be the same as the outer diameter of the inner member; and, preferably, the outer member is formed by drawing such that its inner surface is rough to reduce sliding friction while assuring that the distal cutting end of the inner member is forced against the inner edge of aperture 46. Preferably, the cross sectional configuration of the elongate body 58 of the inner cutting member along the portion in which the opening 60 is disposed is semi-cylindrical ranging from 180° to 22 °, it being important to maintain structural strength of the inner cutting member.

The configuration of the aperture 46 utilizing cylindrically curved surface 154, preferably of a diameter of 3 mm, reduces the thickness of the outer member to permit the probe to be positioned closer to a substance to be cut, directs the substance to be cut centrally inwardly and creates side thicknesses greater than the distal and proximal edge thicknesses to define the cutting are a along the distal edge. Additionally, the use of the conical bore 156 equalizes vacuum force on the substance to be cut while the taper provides an ideal cutting angle for shearing of from 15° to 25°, the diameter of bore 156 being from 3 to 5 mm. The conical surface 160 at the distal end of the inner member preferably has a taper of from 20° to 40° to enhance flow of the cut substance therethrough.

Inasmuch as the present invention is subject to many variations, modifications and changes in detail, it is intended that all subject matter discussed above or shown in the accompanying drawings be interpreted as illustrative and not in a limiting sense.

What is claimed is:

1. A surgical cutting instrument comprising
hub means,
an elongate probe extending from said hub means including
a tubular outer member having a distal end with an aperture in a side wall thereof, and
an inner cutting member slidably disposed in said outer member having a distal end defining a cutting edge positioned at said distal end of said outer member and an elongate body extending from said distal end of said inner cutting member and having a cut away portion running therealong from a position adjacent said cutting edge to said hub means, the cross sectional configuration of said elongate body along said cut away portion being partially cylindrical ranging from 180° to 220°;
drive means for reciprocating said inner cutting member and said outer member relative to each other to move said cutting edge of said inner cutting member back and forth past said aperture in said outer member; and
suction means communicating with said probe adjacent said hub means to remove sustance cut by relative reciprocation of said inner cutting member and said outer member whereby said cut away portion along said elongate body of said inner cutting member provides increased cross sectional flow area along said probe and causes relative reciprocation of said inner cutting member and said outer member to agitate the cut substance to prevent clogging of said probe.

2. A surgical cutting instrument as recited in claim 1 wherein said hub means mounts said outer member of said probe and has a chamber therein through which said inner member of said probe extends, said inner member carrying piston means movable in said chamber with reciprocation of said inner member to increase and decrease pressure in said probe.

3. A surgical cutting instrument as recited in claim 2 wherein said suction means includes a rigid suction tube communicating with said chamber in said hub means and finger operated valve means for controlling the application of suction to said probe.

4. A surgical cutting instrument as recited in claim 3 wherein said rigid tube has a closed end with an opening formed in a side wall adjacent said closed end, and said valve means includes an elastic tubing having an end stretched over said closed end of said rigid tube to seal said opening when no outside force is applied thereto, said tubing being flexed by pressure applied to said tubing at a position opposite said opening in said rigid tube to move said tubing away from said opening.

5. A surgical cutting instrument as recited in claim 4, wherein said drive means includes motor means rotatably driving a shaft axially aligned with said inner cutting member, cam means rotatably driven by said shaft and having a nib projecting therefrom at a position offset from the axis of said shaft and a ball bearing carried by said nib, and cam follower means having a planar surface contacting said ball bearing and arranged in a plane at an angle other than 90° relative to the axis of said shaft and a member extending from said planar surface and having an end engaging said piston carried by said inner cutting member.

6. A surgical cutting instrument as recited in claim 5 wherein said cam follower means includes a square shaft received in a square passage to prevent rotation of said cam follower means.

7. A surgical cutting instrument as recited in claim 6 wherein said inner cutting member has a stem extending through said chamber and protruding beyond the end of said hub means, and said end of said extending member of said cam follower means is hollow to receive said stem.

8. A surgical cutting instrument as recited in claim 1 wherein said drive means includes means for translating rotary movement to reciprocating movement having a reciprocating member with a hollow end, and said inner cutting member of said elongate probe has a stem received in said hollow end of said member.

9. A surgical cutting instrument as recited in claim 1 wherein said aperture in said tubular outer member includes a surface formed by a part of an imaginary cylinder having an axis extending transverse to the longitudinal axis of said outer member and offset therefrom, and an inwardly tapered conical bore.

10. A surgical cutting instrument as recited in claim 9 wherein said distal end of said inner cutting member has a cylindrical cutting head terminating at a peripheral cutting edge.

11. A surgical cutting instrument as recited in claim 1 wherein said inner cutting member is semi-cylindrical in cross section along the portion of said elongate body along which said cut away portion runs.

12. A surgical cutting instrument as recited in claim 1 wherein said inner cutting member is hollow.

* * * * *